United States Patent [19]
Moore

[11] 3,973,696
[45] Aug. 10, 1976

[54] METHOD AND APPARATUS FOR AUTOMATICALLY INJECTING THE FLUID CONTENTS OF A PLURALITY OF PRE-LOADED SYRINGES INTO A GAS CHROMATOGRAPH OR THE LIKE

[75] Inventor: W. Edward C. Moore, Blacksburg, Va.

[73] Assignee: VPI Educational Foundation, Blacksburg, Va.

[22] Filed: July 23, 1975

[21] Appl. No.: 598,515

[52] U.S. Cl. .................................. 222/1; 222/144
[51] Int. Cl.² .................................... B67D 5/60
[58] Field of Search ............... 222/1, 144, 135, 160, 222/162; 221/113, 119, 120, 121, 122

[56] References Cited
UNITED STATES PATENTS

| | | |
|---|---|---|
| 2,158,774 | 5/1939 | Grubelic .......................... 222/144 X |
| 3,066,830 | 12/1962 | Heiss et al. ..................... 222/144 X |

*Primary Examiner*—Allen N. Knowles
*Assistant Examiner*—Hadd Lane
*Attorney, Agent, or Firm*—Seidel, Gonda & Goldhammer

[57] ABSTRACT

An apparatus for sequentially dispensing the fluid contents of a plurality of pre-loaded syringes is disclosed. A first means sequentially places each of a plurality of pre-loaded syringes in a dispensing position, each syringe being of the type having a syringe needle, a syringe barrel and a syringe plunger. A second means depresses the syringe plunger of each syringe located in the dispensing position so as to dispense the fluid contents of each syringe positioned thereat. The first means also removes from the dispensing position any syringe whose plunger has been depressed.

11 Claims, 7 Drawing Figures

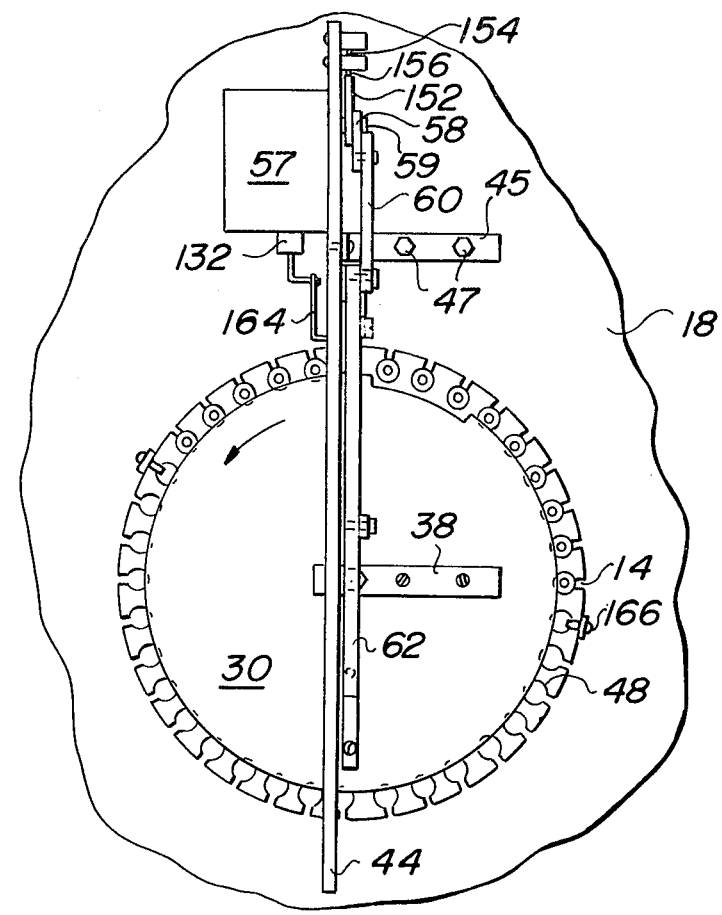
FIG. 3
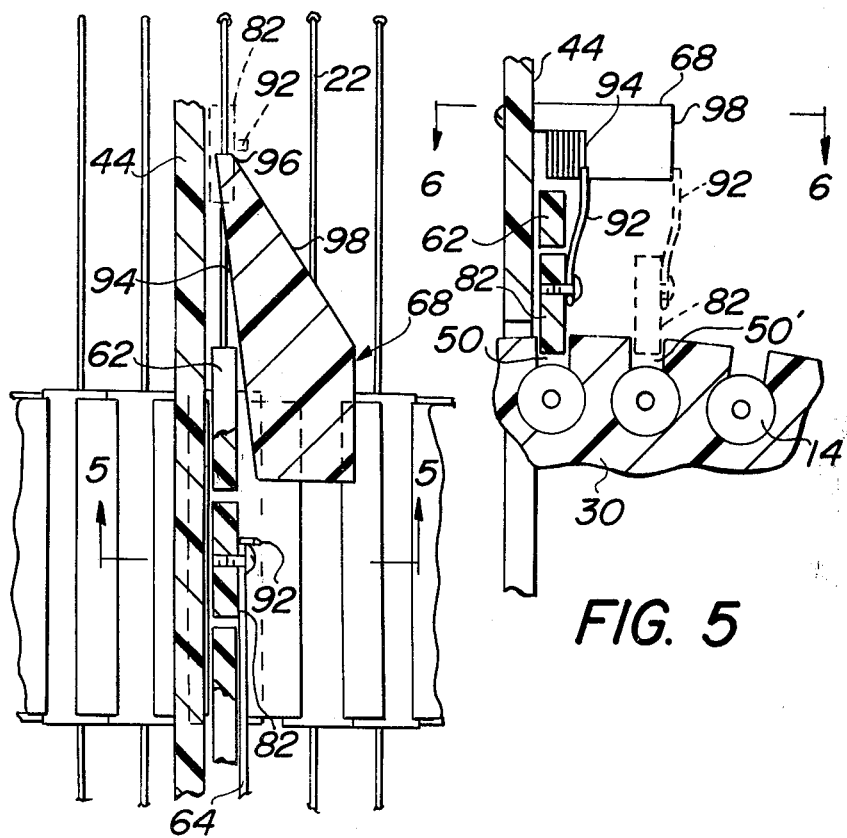
FIG. 6
FIG. 5

METHOD AND APPARATUS FOR AUTOMATICALLY INJECTING THE FLUID CONTENTS OF A PLURALITY OF PRE-LOADED SYRINGES INTO A GAS CHROMATOGRAPH OR THE LIKE

BACKGROUND OF THE INVENTION

The present invention is directed towards an apparatus for dispensing the contents of a plurality of pre-loaded syringes. More particularly, the present invention is directed towards an apparatus for injecting the fluid contents of a plurality of pre-loaded syringes into the receiving port of a gas chromatograph.

Most prior art devices for automatically injecting fluid samples into the receiving port of a gas chromatograph utilize a single syringe in conjection with a plurality of sample containers. In a typical apparatus, a single syringe is inserted into a sample container and the fluid sample therein is drawn into the syringe barrel. The syringe needle is then removed from the sample container and inserted into the receiving port of a gas chromatograph. The plunger of the syringe is then depressed and the fluid contents injected into the chromatograph for analysis.

After the sample has been injected, the syringe needle is withdrawn from the chromatograph and the syringe is flushed with a solvent to prevent contamination of the next sample. The syringe needle is then inserted into a second sample container and the procedure is repeated. The requirement that the syringe be flushed with solvent between each sample injection in the prior art devices has necessitated the utilization of expensive pumps and associated pneumatic controls.

The present invention eliminates the needs for expensive equipment by utilizing a plurality of pre-loaded syringes and a simple electro-mechanical device for injecting the fluid contents of each syringe into a chromatography column. More particularly, in accordance with the present invention a plurality of pre-loaded syringes are placed on a rotary wheel or similar mechanism which intermittently positions each syringe coaxial with the injection port of the chromatograph. As each syringe is brought into alignment with the injection port, a drive arm advances the syringe needle into the injection port and depresses the syringe plunger so as to inject the sample into the chromatography column.

In order to keep the samples in the syringes, prior to the insertion of the syringe needle into the receiving chamber of the chromatograph, the tip of the syringe needle is capped with a coating of a plastic substance such as Tygon (Trademark). During the injection process, the syringe needle penetrates the Tygon coating at the same time as it breaches the outer surface of the septum of the injection port of the chromatograph. After the sample has been injected into the chromatography column, the syringe is withdrawn from the injection port and returned to the rotary wheel and a new pre-loaded syringe is positioned coaxial with the injecting port of the chromatograph.

While the present invention is utilized primarily in conjunction with a gas chromatograph, it may also be utilized with other appropriate sample testing devices.

For the purpose of illustrating the invention, there is shown in the drawings a form which is presently preferred; it being understood, however, that this invention is not limited to the precise arrangements and instrumentalities shown.

BRIEF DESCRIPTION OF THE DRAWINGS

FIG. 3 is an end view of the sample changer shown in FIG. 1.

FIG. 5 is a partial view taken along line 5—5 of FIG. 4.

FIG. 6 is a partial view taken along line 6—6 of FIG. 5.

DETAILED DESCRIPTION OF THE INVENTION

Figure 1:
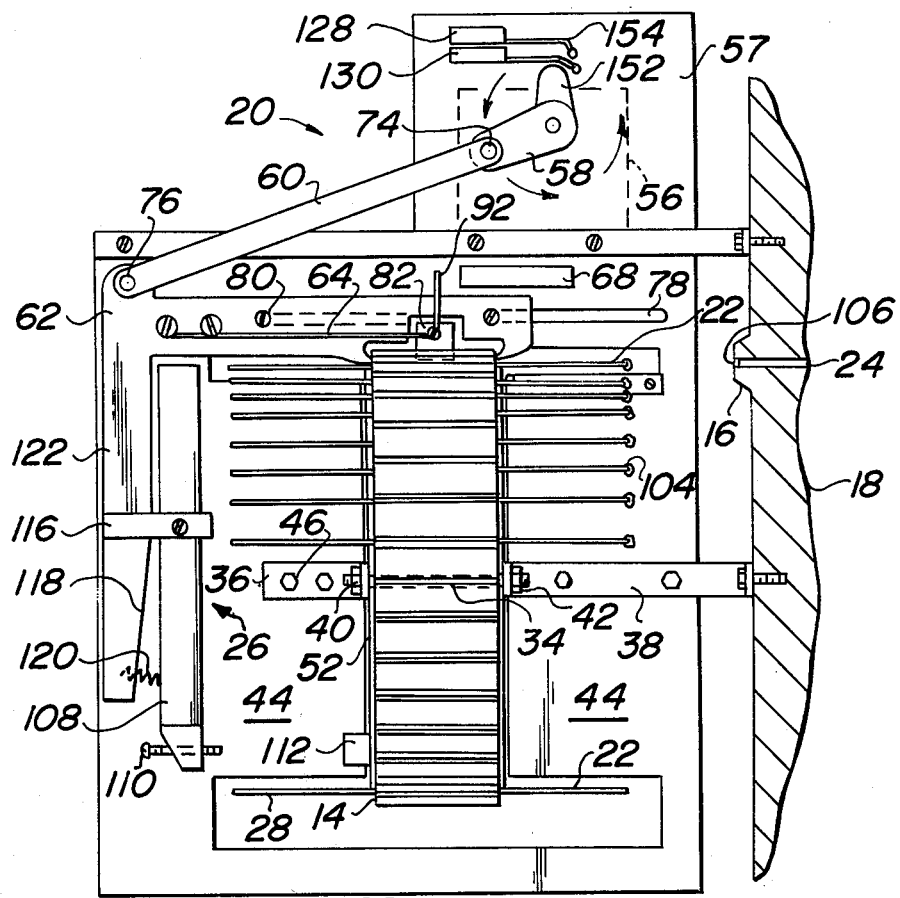
FIG. 1 is a side elevational view of a sample changer constructed in accordance with the principles of the present invention wherein a syringe is in the pre-dispensing position.
Figure 4:
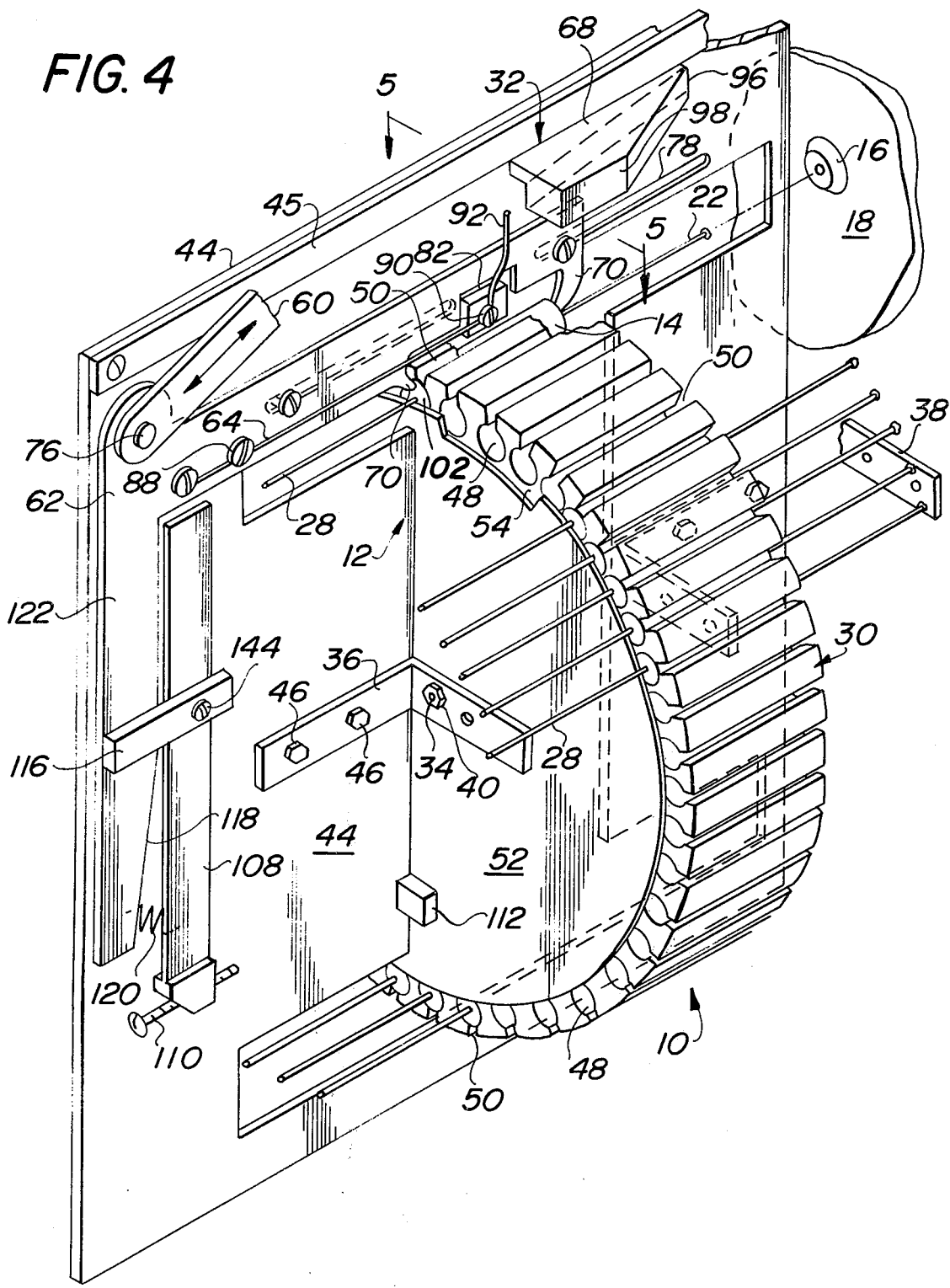
FIG. 4 is a partial cut-away perspective view of the sample changer as shown in FIG. 1.

Referring now to the drawings wherein like numerals indicate like elements, there is shown in FIGS. 1 and 4 a sample changer constructed in accordance with the principles of the present invention and designated generally as 10. Sample changer 10 comprises a means 12 for intermittently positioning a plurality of syringes 14 in a pre-dispensing position coaxial with the injection port 16 of a gas chromatograph 18, motor means 20 for moving each syringe 14 positioned in the pre-dispensing position into a dispensing position wherein its syringe needle 22 is located within the receiving cavity 24 of chromatograph 18, and a means 26 for depressing the syringe plunger 28 of each syringe located in the dispensing position. As will be shown in greater detail below, the means 20 for moving each syringe 14 position in the pre-dispensing position into a dispensing position also returns the syringe to the pre-dispensing position after its fluid contents have been injected into receiving cavity 24.

Means 12 for positioning each of a plurality of syringes 14 in a pre-dispensing position comprises a delivery wheel 30 and a means 32 for intermittently rotating said delivery wheel so as to sequentially place each of the plurality of syringes 14 in the pre-dispensing position. Delivery wheel 30 is rotatably mounted on shaft 34 by suitable bearings (not shown). Shaft 34 is securely mounted on brackets 36 and 38 by nuts 40 and 42 which cooperate with the threaded ends of shaft 34. The entire delivery wheel assembly is secured to support plate 44 by pins 46. Support plate 44 is attached to gas chromatograph 18 by brackets 38, 45 and screws 47 in such a manner that the syringe 14 situated adjacent projections 70 of slide arm 62 is positioned in a pre-dispensing position coaxial with the injection port 16 of chromatograph 18.

Delivery wheel 30 has a plurality of axially oriented apertures 48 therein, each such aperture is adapted to releasably secure one syringe 14 in delivery wheel 30. A channel 50 is associated with each aperture 48 and provides access to the syringe barrels 102 located in apertures 48. A retaining plate 52 is spaced approximately one sixteenth of an inch from the outer surface of delivery wheel 30 and is stationarily supported on support plate 44 via bracket 36. Retaining plate 52 retains syringes 14 in delivery wheel 30 during operation of sample changer 10. A portion 54 of retaining plate 52 is cut out so as to facilitate replacement of empty syringes. See FIG. 4. Empty syringes may be replaced by merely withdrawing them from their associated aperture 48 in the direction from right to left in FIG. 1.

The means 32 intermittently rotates delivery wheel 30 so as to sequentially place each of the plurality of syringes 14 into the pre-dispensing position. Motor means 20 comprises motor 56, linkages 58 and 60, slide arm 62, leaf spring 64, and tab 82. In the preferred embodiment, motor 56 is a 10 RPM motor with magnetic braking capabilities. Such motors are well known in the art and need not be described in detail herein. Motor 56 is mounted within housing 57 which is suitably coupled to support plate 44.

As will be shown in detail below, the operation of motor 56 is controlled by a timing circuit 72 (see FIG. 7) also mounted in housing 57. It is sufficient to state at this point that motor 56 advances a single revolution once every preselected time period determined by timing circuit 72. Whenever a new syringe 14 is to be placed into the pre-dispensing position, motor 56 will be activated to rotated linkage 58 through a single revolution.

Linkage 58 is mounted for rotation about the longitudinal axis of shaft 59 by motor 56. Linkage 58 is connected to slide arm 62 via linkage 60. Pivot pin 74 pivotably connects one end of linkage 60 to linkage 58 and pivot pin 76 pivotably connects the other end of linkage 60 to arm 62. Slide arm 62 is slidably mounted in slots 78 in support plate 44 by suitable slide pins 80. As motor 56 proceeds through a single revolution, slide arm 62 reciprocates back and forth between its rearmost position illustrated in FIG. 1 and its forwardmost position illustrated in FIG. 2 whereupon linkage 58 will cease rotating until motor 56 is again enabled by timing circuit 72.

A tab 82 is connected for movement with slide arm 62 by leaf spring 64 and pins 88 and 90. See FIG. 4. A curved upper portion 92 of leaf spring 64 extends upward beyond pin 90 and is positioned to engage angled guide 68 as slide arm 62 is advanced in the direction of chromatograph 18. It should be noted at this time that when linkage 58 is in the position illustrated in FIG. 1 and slide arm 62 is at its rearmost position, tab 82 is within the channel 50 located between projections 70 of slide arm 62.

The interaction between tab 82, curved upper portion 92 of leaf spring 64 and angled guide 68 can best be understood with reference to FIGS. 5 and 6. As linkage 58 begins rotating in the direction shown in FIG. 1, slide arm 62 is advanced in the direction of chromatograph 18 and curved upper portion 92 of leaf spring 64 engages the inner surface 94 of angled guide 68. The resultant force on portion 92 of leaf spring 64 tends to displace tab 82 in the direction of support plate 44. Movement in that direction is constrained, however, by the counterforce of leaf spring 64 against a side face of arm 62.

Figure 2:
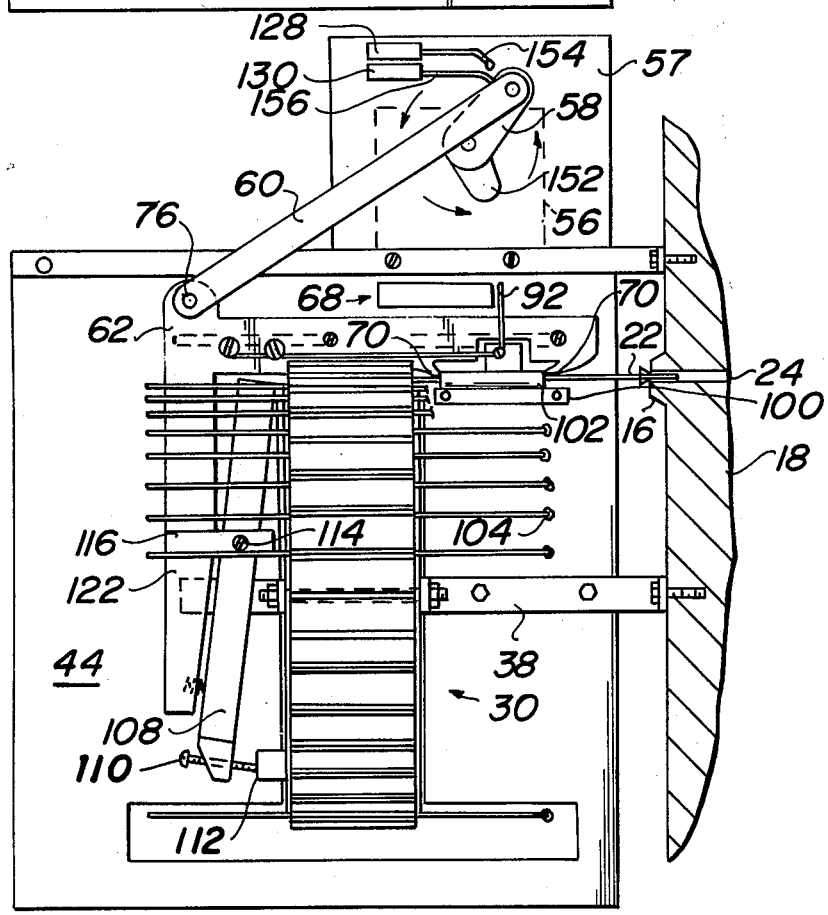
FIG. 2 is a side elevational view of the sample changer of FIG. 1 wherein a syringe is in the dispensing position.

As the linkage 58 continues to rotate, slide arm 62 advances in the direction of chromatograph 18 until it attains the position illustrated in FIG. 2. As slide arm 62 approaches this position, portion 92 of leaf spring 64 clears the forwardmost tip 96 of angled guide 68 and snaps to the phantom position illustrated in FIG. 6. As linkage 58 continues to rotate in a counterclockwise direction, slide arm 62 is drawn away from chromatograph 18 and curved upper portion 92 of leaf spring 64 engages the angled outer surface 98 of angled guide 68. As slide arm 62 continues its rearward translation, leaf spring 64 and tab 82 are drawn into the phantom position illustrated in FIG. 5. The net result of the foregoing is that tab 82 will be transferred from the channel 50 directly below slide arm 62 to the next succeeding channel 50' (FIG. 5). As linkage 58 completes its revolution and slide arm 62 attains its rearmost position, portion 92 of leaf spring 64 clears the rearmost portion of angled guide 68 and the tension in leaf spring 64 causes tab 82 to return to the position illustrated in FIG. 6 thereby positioning the next succeeding syringe 14 in the predispensing position coaxial with injection port 16 of chromatograph 18.

Projections 70 on slide arm 62 are each juxtaposed to an end face of the syringe barrel 102. As best shown in FIG. 4, as a new syringe 14 is moved into the pre-dispensing position by delivery wheel 30, the syringe barrel 102 of the syringe 14 is engaged by projections 70 on slide arm 62. Once a new syringe 14 has been positioned in the pre-dispensing position and motor 56 is enabled by timing circuit 72, slide arm 62 advances in the direction of chromatograph 18. As slide arm 62 advances in this direction, syringe barrel 102 is withdrawn from aperture 48 and engaged by channel guide 100 (see FIG. 2). Syringe barrel 102 will advance along channel guide 100 until syringe 14 attains the dispensing position illustrated in FIG. 2.

It should be noted at this time that the fluid substance within syringe barrel 102 is kept in the syringe prior to injection into receiving cavity 24 by a plastic coating 104 located at the tip of syringe needle 22. In the preferred embodiment, a Tygon coating is used. Other suitable coatings may, however, be utilized without departing from the spirit or scope of the present invention. As best seen in FIG. 2, the tip of the syringe needle 22 pierces plastic coating 104 at the same time as it pierces septum 106 (FIG. 1) of injection port 16.

After a syringe 14 is positioned in the dispensing position, the injector means depresses the syringe plunger 28 of the syringe in the dispensing portion. Means 26 comprises injection arm slide 108 mounted on arm 62, adjustable screw 110, and limit stop 112. Injection arm 108 is pivotally mounted on downward extending portion 122 of slide arm 62 via pivot pin 114 and bracket 116. The forwardmost edge 118 of the downwardly extending portion 122 of slide arm 62 is tapered to permit the clockwise rotation of injection arm 108 as viewed in FIG. 1. Injection arm 108 is normally biased in the position shown in FIG. 1 by compression spring 120 connected between injection arm 108 and the edge 118 of slide arm 62. Adjustable screw 110 is threaded through the lowermost end of injection arm 108 and is disposed to engage limit stop 112.

As best shown in FIG. 2, adjustable screw 110 engages stop 112 and pivots injection arm 108 in a clockwise direction as slide arm 62 approaches its forwardmost position wherein syringe 14 is positioned in the dispensing position. This causes the uppermost end of injection arm 108 to depress the syringe plunger 28 of the syringe 14 located in the dispensing position, thereby injecting the fluid contents in syringe barrel 102 into receiving cavity 24 of chromatograph 18.

After injection arm 108 has depressed the syringe plunger 28 of the syringe 14 in dispensing position, slide arm 62 returns to its rearmost position illustrated in FIG. 1. As slide arm 62 recedes in this direction, the syringe barrel 102 of the syringe located in the dispensing position is returned to the appropriate aperture 48 by projections 70 and tab 66 will cause delivery wheel 30 to rotate in the manner described above.

In summary, when motor 56 is enabled by timing circuit 72, linkage 58 begins rotating in a counterclockwise direction (FIG. 1). Slide arm 62 advances in the direction of chromatograph 18 causing the syringe 14 to leave the pre-dispensing position and advance along channel guide 100. Concurrently, portion 92 of leaf spring 86 engages the inner surface 94 of angled guide 68 and is urged in the direction of support plate 44. As slide arm 62 approaches its foremost position (in FIG. 2), syringe needle 22 of syringe 14 pierces the septum 106 of injection port 16 and enters receiving cavity 24, portion 92 of leaf spring 64 clears the foremost tip 96 of angled guide 68 and jumps to the phantom position illustrated in FIG. 6. At the same time injection arm 108 pivots in the clockwise direction (see FIG. 2) thereby depressing syringe plunger 28 of the syringe 14 located in the dispensing position.

As linkage 58 continues its rotation, the forward motion of slide arm 62 ceases and slide arm 62 begins its rearward movement away from chromatograph 18. As slide arm 62 progresses in this direction, the syringe 14 located in the dispensing position returns to the pre-dispensing position within aperture 48 and portion 92 of leaf spring 64 engages the outer surface 98 of angled guide 68 thereby moving tab 82 into channel 50' (FIG. 5). As slide arm 62 approaches its rearmost position, portion 92 of leaf spring 64 clears angled guide 68 and the tension in leaf spring 64 causes delivery wheel 30 to position the next succeeding syringe 14 in the pre-dispensing position.

Figure 7:
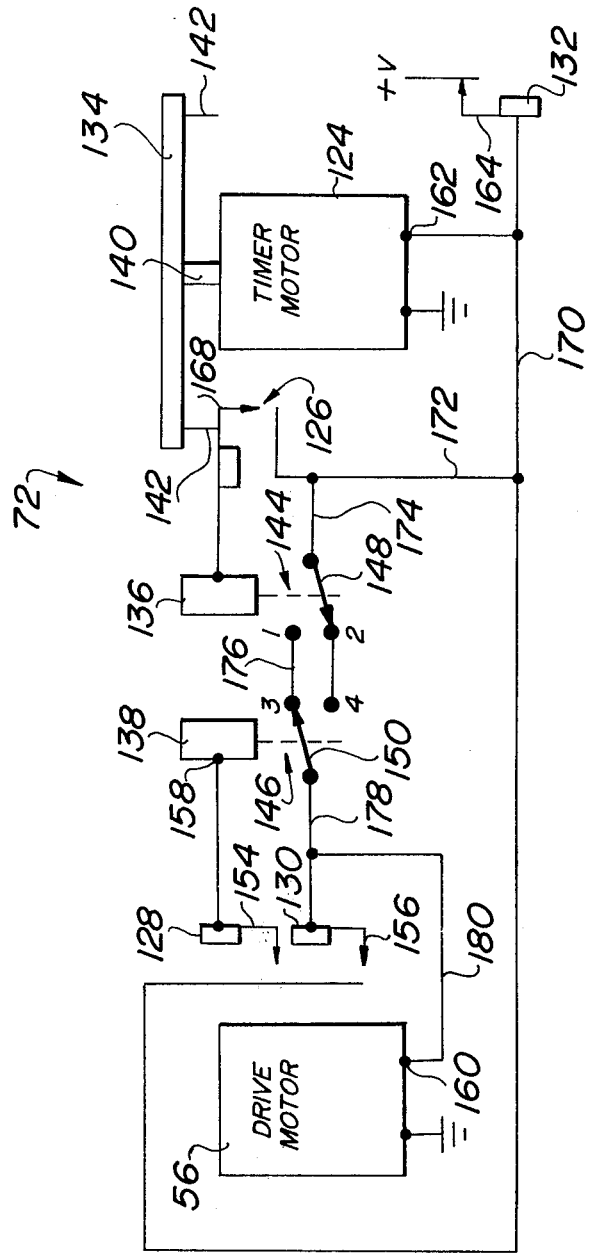
FIG. 7 is a schematic view of a priming circuit utilized in conjection with the sample changer shown in FIG. 1.

The timing circuit for controlling the operation of sample changer 10 is illustrated in FIG. 7. Timing circuit 72 which is connected to motor 56 comprises timer motor 124, normally open microswitches 126, 128 and 130, normally closed microswitch 132, timing wheel 134 and latching relays 136 and 138. The particular intervals at which sample changer 10 will inject a new sample into chromatograph 18 is controlled by timing wheel 134. Timing wheel 134 is connected to the drive shaft 140 of timer motor 124 and is rotated thereby one revolution per unit time such as every two hours. A plurality of pins 142 are inserted around the outer rim of timing wheel 134 at any time interval such as three minute intervals. Hence, 3 minutes will be the intervals between injections. As will be seen below, as timing wheel 134 is rotated by timer motor 124, pins 142 will intermittently close microswitch 126 enabling drive motor 56 and initiating a single revolution of drive motor 56. Accordingly, the fluid contents of a different prefilled syringe 14 will be injected into chromatograph 18 every time a pin 142 closes microswitch 126.

Latching relays 136 and 138 are commercially available and need not be described in detail herein. It is sufficient to state that every time a new pulse of current is applied to either latching relay 136, 138, the relay 136, 138 will causes its associated single throw double pole switch 144, 146, respectively, to latch into a new position. That is, if contact arm 148 is in contact with terminal 2 and a pulse of current is applied to latching relay 136, contact arm 148 will jump to terminal 1 and will stay in that position until a new pulse of current is applied to latching relay 136. Similarly, if contact arm 150 of switch 146 is connected to contact 3 and a pulse of current is applied to latching relay 138, contact arm 150 will switch to contact 4 and will stay in that position until another pulse of current is applied to latching relay 138. Drive motor 56 has been described in detail above and will not be redescribed at this time.

Normally open microswitches 128 and 130 are situated on the outer wall of housing 57 and are positioned so that they are simultaneously activated by cam 152 (FIG. 2) which is secured to main drive shaft 59 of drive motor 56. As can best be seen in FIG. 3, linkages 58 and 60 are laterally disposed from contact arms 154 and 156 of microswitches 128, 130, respectively, and therefore do not make contact therewith upon rotation with drive shaft 59.

Microswitch 128 is connected between normally closed microswitch 132 and input terminal 158 of latching relay 138. Accordingly, whenever cam 152 closes contact arm 154, a pulse of current will be applied to latching relay 138 thereby causing contact arm 150 to toggle. Microswitch 130 is connected between normally closed microswitch 132 and input terminal 160 of drive motor 56. Accordingly, whenever cam 152 closes contact arm 156, current will be applied to input terminal 160 and drive motor 56 will be enabled until cam 52 is past arm 156 of microswitch 130. Microswitch 132 is connected between a power supply of +V volts and input terminal 162 of timer motor 124. As long as normally closed microswitch 132 remains closed, power will be supplied to timer motor 124 and timing wheel 134 will intermittently enable microswitch 126. As can best be seen in FIG. 3, a microswitch 132 is secured to housing 57. Contact arm 164 of microswitch 132 is positioned for engagement with dummy tab 166 which is inserted into channel 50 associated with the aperture 48 immediately following the last aperture containing a syringe 14. See FIG. 3. When the aperture 48 containing the dummy tab 166 enters the pre-dispensing position, it will trip contact arm 164 of microswitch 132 thereby disconnecting the power to timing circuit 72.

The operation of timing circuit 72 can best be described by assuming that delivery wheel 30 is in the position illustrated in FIG. 3 and that cam 152 is in the position illustrated in FIG. 1. Additionally, it will be assumed that contact arms 148 and 150 are in the positions shown in FIG. 7. In this position, sample changer 10 will remain dormant until the next succeeding pin 142 trips contact arm 168 of microswitch 126.

When contact arm 168 is so tripped, a pulse of current will be applied to microswitch 126 and contact arm 148 will switch to contact terminal 1. This will close a circuit between the +V volts power supply and input terminal 160 of drive motor 56 via microswitch 132, conductors 170, 172 and 174, switch 144, conductor 176, switch 146, and conductors 178 and 180. Drive motor 56 will be energized and drive shaft 59 will be free to rotate through a single revolution. The resulting rotation of drive shaft 59 will cause sample changer 10 to proceed through a single dispensing operation as described above. As drive shaft 59 completes a single revolution, cam 152 will simultaneously contact both contact arms 154 and 156 of microswitches 128 and 130, respectively. When contact arm 148 is closed, latching relay 138 will be energized and contact arm 150 will switch to contact terminal 4 breaking the closed circuit between switches 144 and 146. Accordingly, the closed path between the +V volts power supply and the input terminal 160 of drive motor 52 via microswitch 132, conductors 170, 172 and 174, switch 144, conductor 176, switch 146, and conductors 178 and 180 will be broken. Drive motor 56 will remain energized, however, until cam 152 is past contact arm 156 of microswitch 130. That is, as long as cam 152 closes contact arm 156 of microswitch 130, a closed circuit between the +V volts power source and input terminal 160 of drive motor 56 will exist via microswitch 132, conductor 170, microswitch 130, and conductor 180. When contact arm 156 finally disengages from cam 152, no power will be applied to input terminal 160 of drive motor 56 and sample changer 10 will remain dormant until the next succeeding pin 142 enables contact arm 168 of microswitch 126.

The present invention may be embodied in other specific forms without departing from the spirit or essential attributes thereof and, accordingly, reference should be made to the appended claims, rather than to the foregoing specification as indicating the scope of the invention.

What is claimed is:

1. Apparatus for sequentially dispensing the fluid contents of a plurality of pre-loaded syringes of the type having a syringe needle, a syringe barrel, and a syringe plunger comprising:
    first means for supporting a plurality of syringes and for sequentially placing each of said plurality of syringes in a dispensing position;
    second means for depressing the syringe plunger of each syringe positioned in said dispensing position so as to dispense the fluid contents of each said syringe positioned in said dispensing position; and
    said first means being operatively disposed for removing each syringe positioned in said dispensing position from said dispensing position after the syringe plunger of said syringe has been depressed by said second means.

2. Apparatus in accordance with claim 1 wherein said first means comprises:
    third means for sequentially placing each of said syringes in a pre-dispensing position; and
    fourth means for moving each said syringe positioned in said pre-dispensing position into said dispensing position.

3. Apparatus in accordance with claim 2 wherein said third means comprises:
    syringe support means having a plurality of apertures therein, each said aperture adapted to releasably support one said syringe; and
    motor means for intermittently rotating said syringe support means so as to sequentially place each said plurality of syringes in said pre-dispensing position.

4. Apparatus in accordance with claim 3 wherein said means for intermittently rotating said syringe support means includes a timing circuit for controlling the frequency of said intermittent rotations.

5. Apparatus in accordance with claim 4 wherein said timing circuit comprises:
    a timing wheel having a plurality of projections thereon;
    switch means positioned to be tripped by said projections;
    means responsive to the tripping of said switch means for causing said cylindrical syringe support means to rotate through a sufficient arc to position one of said syringes in said pre-dispensing position; and
    motor means for rotating said timing wheel thereby causing said projections to intermittently trip said switch means.

6. Apparatus in accordance with claim 5 wherein said timing wheel includes a plurality of apertures therein, each said aperture being adapted to support a single said projection, and wherein the frequency with which said switching means is tripped may be controlled by placing said plurality of projections in desired said apertures.

7. Apparatus in accordance with claim 3 wherein said fourth means engages each said syringe as it enters said pre-dispensing position, withdraws each said syringe so engaged from said syringe support means and advances each syringe so engaged into said dispensing position.

8. Apparatus in accordance with claim 7 wherein said fourth means also returns each said syringe positioned in said dispensing position from said dispensing position to said predispensing position.

9. Apparatus for automatically dispensing the fluid contents for a plurality of pre-loaded syringes, comprising:
    a support structure;
    cylindrical support means mounted on said support structure and having a plurality of axially oriented apertures therein, each said aperture adapted to releasably support one syringe;
    motor means for intermittently rotating said cylindrical support means a predetermined arc to a pre-dispensing position whereby a different one of said syringes is positioned in said pre-dispensing position after each said intermittent rotation;
    reciprocal means mounted on said support structure for engaging each syringe positioned in a pre-dispensing position and for moving each syringe so positioned in an axial direction into a dispensing position, causing each said syringe positioned in said dispensing position to discharge its fluid contents, and then returning each discharged syringe from said dispensing position to said pre-dispensing position.

10. A method for dispensing the fluid contents of a plurality of pre-loaded syringes of the type having a syringe needle, a syringe barrel and a syringe plunger, said method comprising the steps of:
    selectively placing one of a plurality of syringes in a dispensing position;
    moving said one syringe in an axial direction from said pre-dispensing position into said dispensing position;
    depressing the syringe plunger of said one syringe positioned in said dispensing position so as to dispense the fluid contents thereof;
    removing said one syringe from said dispensing position after said depressing step has been completed;
    then automatically moving a new syringe into a dispensing position.

11. A method in accordance with claim 10 including rotating a common support for said syringes about an axis parallel to the syringes to move the new syringe into the dispensing position.

* * * * *